United States Patent [19]

Berg et al.

[11] Patent Number: 5,780,690
[45] Date of Patent: Jul. 14, 1998

[54] BISPHENOL SYNTHESIS ON MODIFIED ION-EXCHANGE RESINS USING SPECIALLY PURIFIED CARBONYL COMPOUNDS

[75] Inventors: Klaus Berg, Krefeld; Gerhard Fennhoff, Willich; Ralf Pakull, Cologne; Hans-Josef Buysch, Krefeld; Bernhard Wehrle, Langenfeld; Alfred Eitel, Dormagen; Claus Wulff, Krefeld; Jürgen Kirsch, Leverkusen, all of Germany

[73] Assignee: Bayer Aktiengesellschaft, Leverkusen, Germany

[21] Appl. No.: 831,543

[22] Filed: Apr. 8, 1997

Related U.S. Application Data

[63] Continuation of Ser. No. 501,986, Jul. 12, 1995, abandoned.

[30] Foreign Application Priority Data

Apr. 28, 1992 [DE] Germany .............. 42 13 870.1

[51] Int. Cl.$^6$ .................................................. C07C 37/20
[52] U.S. Cl. ........................................ 568/727; 768/724
[58] Field of Search ............................... 568/727, 724

[56] References Cited

U.S. PATENT DOCUMENTS

| 2,182,308 | 12/1939 | Britton et al. | 260/619 |
| 2,191,831 | 2/1940 | Perkins | 260/619 |
| 2,468,982 | 5/1949 | Jansen | 260/619 |
| 2,623,908 | 12/1952 | Stosser et al. | 260/619 |
| 2,775,620 | 12/1956 | Williamson | 260/619 |
| 4,912,263 | 3/1990 | Rudolph et al. | 568/722 |

FOREIGN PATENT DOCUMENTS

| 3619450 | 12/1987 | Germany | 568/719 |

OTHER PUBLICATIONS

Chem Absract No. 3338e, 1962.
Chem. Abstract No. 60 1626h, 1964.
Chem. Abstract No. 59 511h, 1963.
Chem. Abstract No. 58 1403e.

*Primary Examiner*—James H. Reamer
*Attorney, Agent, or Firm*—Joseph C. Gil; Aron Preis

[57] ABSTRACT

The invention relates to a process for the synthesis of bis-(4-hydroxyphenyl)-alkanes on ion-exchange resins or mixtures of ion-exchange resins which are modified with alkyl-SH groups, wherein the monophenols and carbonyl compounds to be used have first been purified to remove substances which can transfer alkyl groups.

5 Claims, No Drawings

BISPHENOL SYNTHESIS ON MODIFIED ION-EXCHANGE RESINS USING SPECIALLY PURIFIED CARBONYL COMPOUNDS

This application is a continuation of application Ser. No. 08/501,986 filed Jul. 12, 1995, now abandoned.

The invention relates to the synthesis of bisphenols from monophenols and carbonyl compounds such as aldehydes and ketones on sulphonic acid ion-exchange systems modified with alkyl-SH groups, wherein the monophenols and carbonyl compounds being used have first been purified to remove accompanying substances which may act as alkylating agents directly or via intermediate compounds.

The condensation of phenols and carbonyl compounds to form bisphenols using various catalysts such as for example hydrochloric acid (U.S. Pat. Nos. 2,182,308 and 2,191,831), boron trifluoride (Chemical Abstracts 58, 3338c), perchloric acid (Chemical Abstracts 60, 1626h), benzenesulphonic acid (Chemical Abstracts 59, 511h), various cation-exchange resins (e.g.GB-PC 842 209, 849 565 and 883 391) and also compounds which contain sulphur as co-catalysts, is well-known (e.g. U.S. Pat. Nos. 2,468,982, 2,623,908, the use of thioglycolic acid and 3-mercaptopropionic acid, from U.S. Pat. No. 2,775,620 the addition of alkyl mercaptans, from Chemical Abstracts 58, 1403e, the addition of hydrogen sulphide). The known co-catalysts which contain sulphur may lead to considerable corrosive damage when operating in practice. The bisphenols prepared using these co-catalysts contain, apart from the unconverted educts such as monophenols and carbonyl compounds, reaction water and condensation products which are isomeric with the desired bisphenol, particularly troublesome, corrosive and discolouring sulphur compounds, which may only be removed with difficulty.

In contrast, the synthesis of bisphenols with sulphonic acid ion-exchange materials moistened with phenol, in which co-catalytically active alkyl-SH groups are fixed on the matrix, e.g. by aminoalkyl mercaptan units in accordance with DE-A 3 619 450 or by thiazoline units in accordance with DE-A 3 727 641, allows the preparation and isolation of very pure bisphenols.

The alkyl-SH groups (e.g. $C_2$–$C_6$ alkyl, preferably $C_4$ alkyl) in this type of resin system may also be covalently bonded either to the polystyrene matrix or partly to the —$SO_3H$ groups in the ion-exchange material. Furthermore, there may also be a mixture of any composition of pure sulphonic acid ion-exchange resin and a resin with exclusively covalently or ionically bonded alkyl-SH groups.

When preparing bisphenols from monophenols and carbonyl compounds such as aldehydes and ketones in accordance with DE-A 36 19 450 and DE-A 37 27 641, however, a rapid decrease in the reactivity and selectivity of the catalyst is noted, even after relatively short production phases, so that the catalyst system being used must be either regenerated or even replaced completely. This leads to production stoppages and additional expenditure in maintaining the production plants.

It has now been found that the catalyst action can be maintained for considerably longer, the space/time yields and purity of the bisphenol and the selectivity of the reaction can be improved if the monophenols and carbonyl compounds used as educts are purified by removing compounds which act as alkylating agents.

The invention relates to a process for the preparation of bis-(4-hydroxyphenyl)-alkanes from monophenols and carbonyl compounds using ion-exchange materials or mixtures of ion-exchange materials, which contain sulphonic acid groups up to 11.5 mol-% which have been modified with 2-aminoethyl mercaptan characterised in that the monophenols and carbonyl compounds used contain alkylating substances of the formula $$R—X$$

wherein

X represents OH, halogen, carboxylate, sulphate or sulphonate and

R may be an open-chain, branched or unbranched, saturated or unsaturated $C_1$–$C_6$ alkyl radical or a $C_5$–$C_7$ cyclic substituted or unsubstituted, saturated or unsaturated alkyl radical, in amounts of less than 0.1%, preferably 0.05, particularly preferably 0.01%.

Alkylating substances in the context of the invention are, for example, alcohols, alkyl halides, alkyl carboxylates, alkyl sulphates and alkyl sulphonates.

Alcohols in the context of the invention are, for example, methanol, ethanol, isomers of propanol, isomers of butanol, long-chain, branched or unbranched homologues, unsaturated alcohols such as, for example, allyl alcohol, cyclic saturated or unsaturated alcohols such as for example cyclopentanol, cyclohexanol or cyclohexenol or polyhydric alcohols such as for example ethylene glycol, 1,2-propylglycol, 1,3-propylglycol or glycerine.

Such compounds are generally present in variable amounts in the educts for the synthesis.

Purification of the educts before reaction may be performed using the usual methods such as, for example, distillation, recrystallisation or extraction or by using molecular sieves, wherein the amounts of these compounds remaining should be <0.1 or <0.05, particularly preferably <0.01%.

EXAMPLE 1

125 g of ion-exchange material (Lewatit SC 102, Bayer AG) moistened with phenol, whose sulphonic acid groups have been occupied up to 11.5 mol-% by 2-aminoethyl mercaptan, are suspended in 499 g of phenol. Then 29 g of acetone (with 0.2% $H_2O$, 0.01% MeOH) are added to the batch, which has been thermostatted at 65° C., and stirred for 4 hours. Subsequently, the acetone conversion is determined by measuring the residual acetone concentration by the ketoxime method (see Table 1). The procedure is repeated 20 times. Before each new batch, the ion-exchange material was filtered off and rinsed with small amounts of phenol until free of product. Then the conversion activity of the ion-exchange material is measured again (see Table 1).

EXAMPLE 2

This is the same as example 1, except that 5,000 ppm of methanol per batch were added, relative to the phenol used.

EXAMPLE 3

This is the same as example 1, except that 5,000 ppm of 2-propanol were added, relative to the phenol used.

The conversion activity (conversion of acetone) of the ion-exchange material used after 20 batches is listed in Table 1 for the three examples.

TABLE 1

Activity of ion-exchange material in examples 1 to 3 (acetone converted)

|  | after 1 batch | after 20 batches |
|---|---|---|
| Example 1 | 99.5% | 98.7% |
| Example 2 | 98.5% | 43.5% |
| Example 3 | 98.9% | 75.2% |

All %-values in all examples are % by weight, if not otherwise marked.

We claim:

1. A process for synthesizing a bis-(4-hydroxyphenyl)-alkane comprising reacting a monophenol with a carbonyl compound selected from the group consisting of aldehyde and ketone in the presence of a sulphonic acid groups-containing ion-exchange material, wherein up to 11.5 mol-% of said groups are occupied by 2-aminoethyl mercaptan, characterized in that said monophenol and carbonyl compound first undergo purification to limit the content of alkylating substances in said monophenol and carbonyl compound to a positive amount of less than 0.01% relative to their weight, wherein said alkylating substances is at least one member selected from the group consisting of methanol, ethanol, 1,2-propanol, 1,3-propanol, isomers of butanol and cyclohexanol, said purification consisting of at least one of distillation, recrystallization, extraction and using molecular sieves.

2. In the process for synthesizing a bis-(4-hydroxyphenyl)-alkane comprising reacting a monophenol with a carbonyl compound selected from the group consisting of aldehyde and ketone in the presence of an ion-exchange resin the improvement comprising (i) purifying said monophenol and carbonyl compound to limit their content of alkylating substances to a positive amount of less than 0.01% relative to their weight, and (ii) using an ion exchange resin which contains sulphonic acid groups wherein up to 11.5 mol-% of said groups are occupied by 2-aminoethylmercaptan, wherein said alkylating substances is at least one member selected from the group consisting of methanol, ethanol, 1,2-propanol, 1,3-propanol, isomers of butanol and cyclohexanol, and wherein said purifying is by distillation, recrystallization, extraction or using molecular sieves.

3. A process for synthesizing a bis-(4-hydroxyphenyl)-alkane comprising reacting a monophenol with a acetone in the presence of a sulphonic acid groups-containing ion-exchange material, wherein up to 11.5 mol-% of said groups are occupied by 2-aminoethyl mercaptan, characterized in that said monophenol and acetone first undergo purification to limit the content of alkylating substances in said monophenol and acetone to a positive amount of less than 0.01% relative to their weight, wherein said alkylating substances is at least one member selected from the group consisting of methanol, ethanol, 1,2-propanol, 1,3-propanol, isomers of butanol and cyclohexanol, said purification consisting of at least one of distillation, recrystallization, extraction and using molecular sieves.

4. In the process for synthesizing a bis-(4-hydroxyphenyl)-alkane comprising reacting a monophenol with acetone in the presence of an ion-exchange resin the improvement comprising (i) purifying said monophenol and acetone to limit their content of alkylating substances to a positive amount of less than 0.01% relative to their weight, and (ii) using an ion exchange resin which contains sulphonic acid groups wherein up to 11.5 mol-% of said groups are occupied by 2-aminoethylmercaptan, wherein said alkylating substances is at least one member selected from the group consisting of methanol, ethanol, 1,2-propanol, 1,3-propanol, isomers of butanol and cyclohexanol, and wherein said purifying is by distillation, recrystallization, extraction or using molecular sieves.

5. In the process for synthesizing a bis-(4-hydroxyphenyl)-alkane comprising reacting a monophenol with acetone in the presence of an ion-exchange resin the improvement comprising (i) purifying said monophenol and said acetone to limit their content of alkylating substance to a positive amount of less than 0.01% relative to their weight, and (ii) using an ion exchange resin which contains sulphonic acid groups wherein up to 11.5 mol-% of said groups are occupied by 2-aminoethylmercaptan, wherein alkylating substance is alcohol selected from the group consisting of methanol, ethanol, 1,2-propanol, 1,3-propanol, isomers of butanol and cyclohexanol, and wherein said purifying is by distillation, recrystallization, extraction or using molecular sieves.

* * * * *